United States Patent [19]

Holmberg et al.

[11] Patent Number: 4,831,176
[45] Date of Patent: May 16, 1989

[54] ETHER PHOSPHONATE SURFACTANTS HAVING BRANCHED HYDROPHOBIC TAILS AND THEIR USE IN AN ENHANCED OIL RECOVERY PROCESS

[75] Inventors: Krister Holmberg, Mölndal; Eva Österberg, Gothenburg, both of Sweden

[73] Assignee: Berol Kemi AB, Stenungsund, Sweden

[21] Appl. No.: 139,832

[22] Filed: Dec. 30, 1987

[30] Foreign Application Priority Data

Jan. 27, 1987 [NO] Norway .................................. 870339

[51] Int. Cl.$^4$ ................................................ C07F 9/38
[52] U.S. Cl. .................................. 558/186; 252/8.551; 252/8.554
[58] Field of Search ........................................... 558/186

[56] References Cited

U.S. PATENT DOCUMENTS

| | | | |
|---|---|---|---|
| 4,316,810 | 2/1982 | Barnham et al. | 252/8.551 |
| 4,319,636 | 3/1982 | Kudchadker et al. | 252/8.554 |
| 4,468,335 | 8/1984 | Chen et al. | 166/274 |
| 4,787,994 | 11/1988 | Thorne et al. | 252/8.551 |

*Primary Examiner*—Jacqueline V. Howard
*Attorney, Agent, or Firm*—Watson, Cole, Grindle & Watson

[57] ABSTRACT

Novel ether phosphonate surfactants having a branched hydrophobic tail are used in a process for enhanced oil recovery from a subterranean oil reservoir. They combine a high oil-mobilizing capacity with a good tolerance against divalent ions. The ether phosphonate surfactants are summarized by the formula

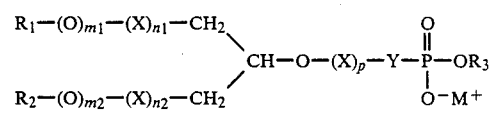

where $R_1$ and $R_2$, being the same or different, are hydrocarbons containing 3–18 carbon atoms each and optionally containing functional groups such as ether and hydroxyl; X is an alkyleneoxy group derived from an alkylene oxide having 2–3 carbon atoms; Y is an alkylene group having 1–4 carbon atoms; $R_3$ is an alkyl group having 1–4 carbon atoms; $M^+$ is a monovalent cation; $n_1$ and $n_2$, being the same or different, are a number from 0 to 4; $m_1$ and $m_2$, being the same or different, are 0 or 1, both $m_1$ and $m_2$ not being 0 at the same time and $m_1$ being 1 when $n_1$ is a number from 1 to 4 and $m_2$ always being 1 when $n_2$ is a number from 1 to 4; and p is a number from 0 to 10.

7 Claims, No Drawings

ETHER PHOSPHONATE SURFACTANTS HAVING BRANCHED HYDROPHOBIC TAILS AND THEIR USE IN AN ENHANCED OIL RECOVERY PROCESS

The present invention relates to a surface active compound which forms microemulsions with a very high solubilizing capacity without the use of a cosurfactant. The surface active compound and the microemulsion containing said surface active compound is suitable for use in enhanced oil recovery.

Microemulsions have been known for a long time. The term was coined by Schulman in 1943 and since that time a substantial amount of literature dealing with various aspects of microemulsions has appeared. (For a review, see L. M. Prince, Microemulsions, Academic Press, New York 1977).

Microemulsions are made from water, an oil component and a surfactant system. The surfactant system traditionally consists of a true surfactant (in the following referred to as "surfactant") and a cosurfactant. The surfactant may be anionic, nonionic, cationic or amphoteric. The cosurfactant (which is sometimes referred to as cosolvent or solubilizing agent) is normally an alkanol having from 3 to 6 carbon atoms, but other types of compounds, such as glycol ethers and amines, may also be used. The cosurfactant is usually a considerably smaller molecule than the surfactant and its role is to affect the molecular packing at the droplet interface in such a way that formation of microemulsion is energetically favoured.

One of the most interesting application areas for microemulsions is surfactant flooding for enhanced oil recovery. Surfactant flooding means injection of a surfactant solution or a microemulsion into a reservoir with a view to decreasing the oil-water interfacial tension and, as a consequence, increase the amount of oil recovered by flooding.

In high surfactant concentration systems a middle phase microemulsion in equilibrium with excess oil and brine forms if the surfactant system is well balanced. The existence of the middle phase microemulsion is considered a necessary condition in order to obtain a satisfactory oil recovery. The microemulsion phase gives an extremely low interfacial tension against brine, as well as oil. It has the ability to mobilize oil blocked in narrow pores, it causes coalescence of oil droplets and it ultimately brings about formation of a continuous oil bank which is pushed forward towards the production hole by a water slug.

The formation and preservation of a microemulsion is, consequently, of utmost importance for a successful result in chemical flooding. However, microemulsions are known to be sensitive to changes in composition. They normally only exist within fairly narrow intervals with regard to surfactant to cosurfactant ratio. During the flooding process a certain degree of separation between the surfactant and cosurfactant is likely to occur. This separation may be caused either by one of the components adsorbing more strongly to the surface of the formation than the other, or by unequivalent distribution of the two components between the oil and brine phases. A change in composition due to selective precipitation or degradation of one the components is also conceivable. Consequently, even with well balanced systems showing only minor differences between the components with regard to adsorption and distribution between the phases a gradual change of system composition will take place and the microemulsion will eventually break. Since the distances to be covered by a microemulsion in chemical flooding are often very long, the long-term preservation of the optimum system is regarded as a major issue for the use of the surfactant flooding technique for enhanced oil recovery.

A number of microemulsions based on anionic surfactants containing one hydrophobic chain and one hydrophilic part have been suggested for use in enhanced oil recovery. For example, the German patent application No. 34 07 565, published on 5/9/85 discloses the use of phosphonate surfactants having one large hydrocarbon group.

However, these phosphonate surfactants require a cosurfactant in order to form the desired middle phase microemulsion with oil and brine. As mentioned before, the use of a surfactant-cosurfactant combination will invariably result in a gradual change in system composition during the flooding process and, consequently, give poor performance in terms of oil recovery.

It has recently been shown that the problem of component separation can be avoided by using certain branched surfactants which form microemulsions without the addition of a cosurfactant. Surfactants with a branched hydrophobic tail and a sulphonate end group have been found to have a high capacity to mobilize oil and have been suggested for use in enhanced oil recovery (U.S. Pat. Nos. 4,446,079; 4,468,335; 4,468,342 and 4,545,912). These surfactants work well in low salinity reservoirs. With high and medium salinity brine, however, problems arise due to precipitation with calcium and magnesium ions.

We have now found that certain novel ether phosphonate surfactants having a branched hydrophobic tail are especially suitable to be used in a process for enhanced oil recovery from a subterranean oil reservoir and combine an unusually high oil-mobilizing capacity with a good tolerance to divalent cations, such as calcium and magnesium ions. At medium and high brine salinity they are considerably more efficient in recovering oil from experimental cores than the corresponding sulphonate surfactants.

When injecting an aqueous solution of the novel surfactants into an oil reservoir they will form a large middle phase microemulsion in equilibrium with excess oil and brine. At equilibrium the surfactants are mainly localized in the middle phase microemulsion and their concentration in both the brine phase and the oil phase is very low. This is a necessary condition to keep the need of surfactants on a low level. Preferably the surfactants are used as the only surfactant and without any cosurfactants although the use of additional surfactants and cosurfactants are within the scope of this invention. In order to increase the solubility of the surfactants in the aqueous injection media the surfactants could be added in the form of an inorganic or organic ammonium salt or combined with a solubilizing agent, such as a lower alcohol or a lower monoalkyl ethylene glycol ether.

The surfactants of the present invention have the general formula

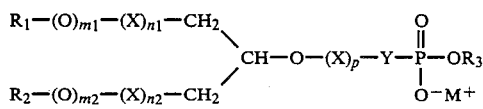

where $R_1$ and $R_2$, being the same or different, are hydrocarbons containing 3–18 carbon atoms each and optionally containing functional groups such as ether and hydroxyl; X is an alkyleneoxy group derived from an alkylene oxide having 2–3 carbon atoms; Y is an alkylene group having 1–4 carbon atoms; $R_3$ is an alkyl group having 1–4 carbon atoms; $M^+$ is a monovalent cation; $n_1$ and $n_2$, being the same or different, are a number from 0 to 4; $m_1$ and $m_2$, being the same or different, are 0 or 1, both $m_1$ and $m_2$ not being 0 at the same time and $m_1$ being 1 when $n_1$ is a number from 1 to 4 and $m_2$ always being 1 when $n_2$ is a number from 1 to 4; and p is a number from 0 to 10. Preferably $R_1$ and $R_2$ are hydrocarbon groups having 6 to 16 carbon atoms. Example of such groups are straight chain or branched hexyl, octyl, nonyl, decyl, undecyl, dodecyl, tridecyl, tetradecyl, hexadecyl, and phenyl, butylphenyl, dibutylphenyl, octylphenyl, and nonylphenyl. The hydrocarbon groups $R_1$ and $R_2$ may also contain one or more double bounds. Preferred groups are branched alkyl groups such as 2-ethylhexyl and other alkyl groups derived from oxo-alcohols. The value of p is preferably 1–5, and the total sum of $n_1+n_2+p$ is preferably 2–10. X is ethyleneoxy, propyleneoxy or butyleneoxy derived from ethylene oxide, propylene oxide or butylene oxide. Preferably X is an ethyleneoxy group. By a proper selection of the type of alkyleneoxy group, the number of such groups and the size of the hydrophobic groups $R_1$ and $R_2$ it is easy to regulate the HLB-balance of the surfactants. The cation $M^+$ is normally an alkali metal ion, an ammonium ion or an organic ammonium ion, such as a primary, secondary, tertiary or quaternary ammonium ion. The organic groups are preferably alkyl or hydroxyalkyl groups having 1–4 carbon atoms, such as metyl, ethyl or hydroxyethyl groups.

The surfactants of the present invention can be prepared by known synthesis methods. A typical procedure is outlined below

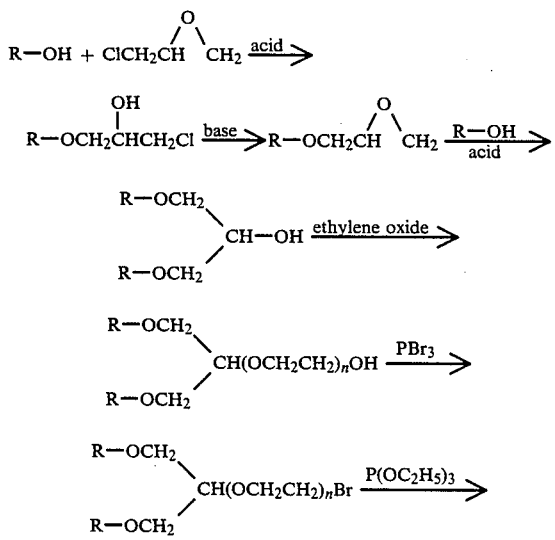

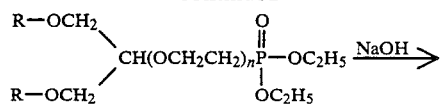

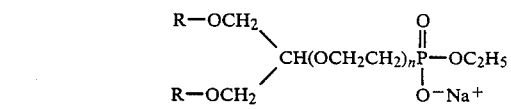

Instead of using ROH as a starting compound it is also possible to expoxidize the compound $RCH_2CH=CH_2$. The first two steps in the reaction procedure above will be replaced by the reaction step.

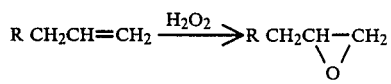

In the above formulae R has the meaning of $R_1$ and $R_2$.

All the above reaction steps are well known in the field of surfactant synthesis. The starting alcohol, ROH, may be a normal alcohol or an alkoxylated alcohol.

The invention is further illustrated by the examples below.

EXAMPLE 1

In this example a comparison is made between an ether phosphonate and an ether sulphonate surfactant based on the same branched hydrophobic tail.

The following ethoxylate was synthesized:

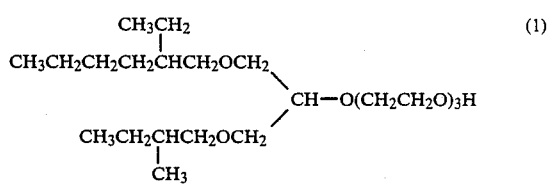

The synthesis procedure comprised reaction between 2-ethyl hexanol and epichlorohydrin using $SnCl_4$ as catalyst (4 h, 80° C.), conversion of the chlorohydrin formed to the glycidol derivative by treatment with NaOH, reaction with 2-methyl butanol (4 h, 80° C.) using $SnCl_4$ as catalyst and subsequent ethoxylation with ethylene oxide to form, on average, a triethylene glycol chain.

The ethoxylate, 1, was converted into the phosphonate, 2, by reaction with $PBr_3$ (6 h, 140° C.) followed by treatment with triethylphosphite (12 h, 90° C.) and subsequent alkaline hydrolysis (2M NaOH, 2 h, 80° C.).

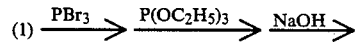

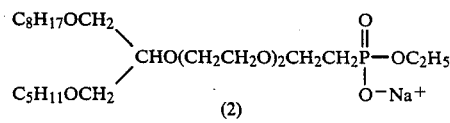

The ethoxylate, 1, was also converted into the sulphonate, 3, by reaction with $SOCl_2$ followed by treatment with $Na_2SO_3$ in a 4:1 mixture of water and diethylene glycol (8 h, 160° C.).

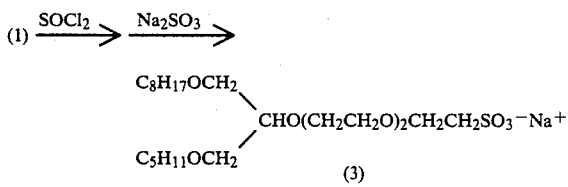

A Berea sandstone core, 10 cm long and 4 cm in diameter, having a permeability of 400 mDarsey was flooded to residual oil saturation with 6% brine at 25° C. A 0.30 pore volume slug containing 2% surfactant was injected followed by continuous injection of brine. With the phosphonate surfactant, 2, 45% of the residual oil was produced within one pore volume of the start of injection. The corresponding figure for the sulphonate surfactant, 3, was 25%.

EXAMPLE 2

In this example a comparison is made between an ether phosphonate according to the present invention, 4, and a conventional ether phosphonate, 5.

An ether phosphonate having a branched hydrophobic tail was synthesized as follows: Phenol was reacted with ethylene oxide to form ethylene glycol monophenyl ether which was subsequently reacted with 1-decene oxide. The alcohol formed was ethoxylated to give, an average, a tetraethylene glycol chain. The ethoxylate was reacted with paraformaldehyde and SOCl$_2$ (1 h, 50° C.) to form the corresponding chloromethyl compound which was treated with triethylphosphite and hydrolyzed with NaOH as in Example 1.

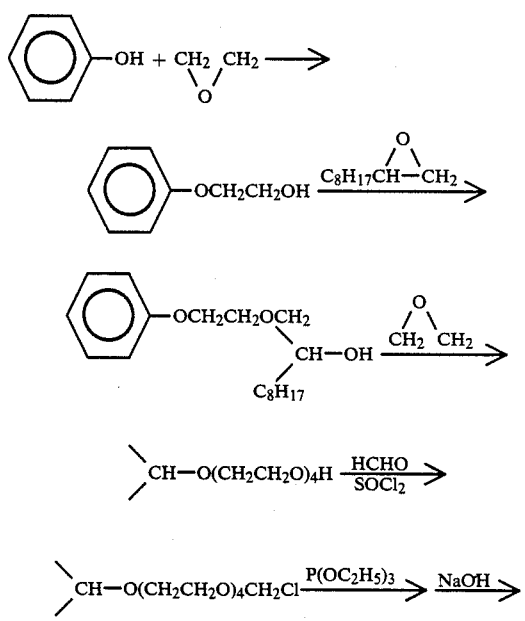

A conventional ether phosphonate surfactant, 5, was synthesized by a similar procedure: Nonyl phenol was ethoxylated with ethylene oxide to form, on average, a hexaethylene glycol chain. The ethoxylate was reacted with paraformaldehyde and SOCl$_2$ to form the chloromethyl compound which was then treated with triethylphosphite and subsequently hydrolyzed with NaOH as in Example 1.

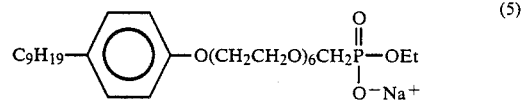

The same Berea sandstone core as in Example 1 was flooded with 8% brine to residual oil saturation at 25° C. A 0.25 pore volume slug containing 3% surfactant was injected followed by continuous injection of brine. With the phosphonate surfactant, 4, in the form of its triethanol ammonium salt, 55% of the residual oil was produced within one pore volume of the start of injection. With the conventional phosphonate surfactant, 5, the oil recovery was less than 5% within one pore volume. Addition of 5% 2-butanol as cosurfactant to the phosphonate, 5, raised the yield of oil recovered to 15%.

EXAMPLE 3

The following phosphonate surfactants were synthesized according to the procedure outlined in Example 1 and Example 2.

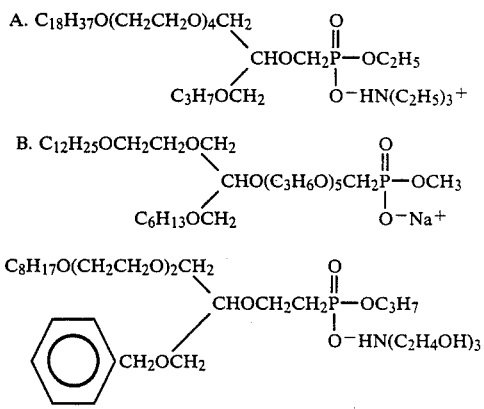

Surfactants A, B, and C were evaluated in the same type of flooding experiment as described in Example 1, The following percentage of residual oil were obtained within one pore volume of the start of the injection.

| Surfactant | Oil produced (%) |
| --- | --- |
| A | 38 |
| B | 40 |
| C | 34 |

We claim:
1. A compound having the formula

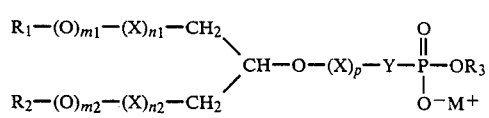

where $R_1$ and $R_2$, being the same or different, are hydrocarbons containing 3–18 carbon atoms each and optionally containing functional groups such as ether and hydroxyl; X is an alkyleneoxy group derived from an alkylene oxide having 2–3 carbon atoms; Y is an alkylene group having 1–4 carbon atoms; $R_3$ is an alkyl group having 1–4 carbon atoms; $M^+$ is a monovalent cation; $n_1$ and $n_2$, being the same or different, are a number from 0 to 4; $m_1$ and $m_2$, being the same or different, are 0 or 1, both $m_1$ and $m_2$ not being 0 at the same time and $m_1$ being 1 when $n_1$ is a number from 1 to 4 and $m_2$ always being 1 when $n_2$ is a number from 1 to 4; and p is a number from 0 to 10.

2. A compound of claim 1, in which $R_1$ and $R_2$ are hydrocarbon groups containing 6–16 carbon atoms.

3. A compound of claim 1 or 2, in which p is a number from 1 to 5 and the sum of $n_1+n_2+p$ is 2–10.

4. A process for recovering oil from a subterranean oil reservoir comprising the step of contacting the subterranean oil with an aqueous medium containing a compound having the formula

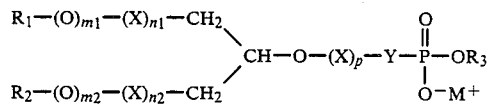

where $R_1$ and $R_2$, being the same or different, are hydrocarbons containing 3–18 carbon atoms each and optionally containing functional groups such as ether and hydroxyl; X is an alkyleneoxy group derived from an alkylene oxide having 2–3 carbon atoms; Y is an alkylene group having 1–4 carbon atoms; $R_3$ is an alkyl group having 1–4 carbon atoms; $M^+$ is a monovalent cation; $n_1$ and $n_2$, being the same or different, are a number from 0 to 4; $m_1$ and $m_2$, being the same or different, are 0 or 1, both $m_1$ and $m_2$ not being 0 at the same time and $m_1$ being 1 when $n_1$ is a number from 1 to 4 and $m_2$ always being 1 when $n_2$ is a number from 1 to 4; and p is a number from 0 to 10.

5. The process of claim 4, wherein $R_1$ and $R_2$ are hydrocarbon groups containing 6–16 carbon atoms.

6. The process of claim 4 or 5, wherein p is a number from 1 to 5 and the sum of $n_1+n_2+p$ is 2–10.

7. The process of claim 4 or 5, wherein the compound is in the form of ammonium salt or an organic ammonium salt.

* * * * *